United States Patent
Wong

(10) Patent No.: US 6,613,550 B2
(45) Date of Patent: Sep. 2, 2003

(54) MICROBIAL PROCESS FOR PREPARATION OF OPTICALLY ACTIVE 3-HYDROXYPYRROLIDINE DERIVATIVES

(75) Inventor: John W. Wong, East Lyme, CT (US)

(73) Assignee: Pfizer Inc., New York, NY (US)

( * ) Notice: Subject to any disclaimer, the term of this patent is extended or adjusted under 35 U.S.C. 154(b) by 270 days.

(21) Appl. No.: 09/796,278

(22) Filed: Feb. 28, 2001

(65) Prior Publication Data

US 2002/0025567 A1 Feb. 28, 2002

Related U.S. Application Data

(60) Provisional application No. 60/186,080, filed on Feb. 29, 2000.

(51) Int. Cl.$^7$ .............................. C12P 17/10; C12P 1/04; C12P 1/02
(52) U.S. Cl. ........................ 435/121; 435/170; 435/171; 435/195; 435/252.1; 435/253.5; 435/254.3; 435/256.1
(58) Field of Search ................................. 435/121, 170, 435/171, 252.1, 254.3, 256.1, 253.5, 195

(56) References Cited

FOREIGN PATENT DOCUMENTS

| | | |
|---|---|---|
| EP | 452143 | 10/1991 |
| EP | 692471 | 1/1996 |
| EP | 1002871 | 5/2000 |
| JP | 61063652 | 4/1986 |
| JP | 1141600 | 6/1989 |
| JP | 5279326 | 5/1993 |
| JP | 9263578 | 10/1997 |

OTHER PUBLICATIONS

Hasegawa, J., et al., *Enantiomer*, 2: 311–314, 1997.
Li, Z., et al., *Tetrahedron: Asymmetry*, 10: 1323–1333, 1999.
Parshikov, I., et al., *Chemistry of Heterocyclic Compounds*, 28(2): 159–162, 1992.

Primary Examiner—Herbert J. Lilling

(74) *Attorney, Agent, or Firm*—Peter C. Richardson; Gregg C. Benson; Gabriel L. Kleiman

(57) ABSTRACT

The present invention is directed to a process for the production of compounds of the formula:

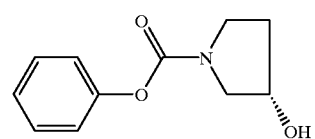

II or

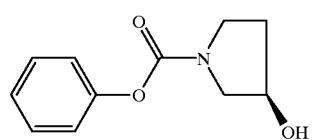

III from a compound of the formula

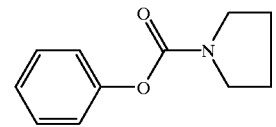

I comprising hydroxylating a compound of the formula I in the presence of an enzyme produced by a microorganism of the genera Cunninghamella species or Aspergillus.

Preferred microorganisms are *Cunninghamella echinulata* var. elegans and *Aspergillus flavipes*.

Mixtures of compounds of formulae II and III may also be highly enriched in their composition of compound II by using the enzyme from *Cunninghamella echinulata* ATC 8688b.

13 Claims, No Drawings

MICROBIAL PROCESS FOR PREPARATION OF OPTICALLY ACTIVE 3-HYDROXYPYRROLIDINE DERIVATIVES

This application claims benefit of Ser. No. 60/186,080 filed Feb. 29, 2000.

BACKGROUND OF THE INVENTION

Several methods have been disclosed for the preparation of optically active 3-hydroxypyrrolidine derivatives. Some of these methods involve the resolution of racemic 3-hydroxypyrrolidine derivatives by the formation of salts with optically active organic acids. Japanese Pat. Appl. Nos. 96-103965, 92-77749, and 84-185583 all describe processes for the resolution of racemic 3-hydroxypyrrolidine derivatives with optically active organic acids. Enzymatic processes have also been disclosed for the resolution of racemic 3-hydroxypyrrolidine derivatives (Hasegawa, et al, Enantiomer, 2(3–4): 311–314 (1997); Jap Pat. Appl. No. 87-301052). These enzymatic methods involve the stereoselective hydrolysis of racemic N-benzyl-3-acyloxypyrrolidines with hydrolytic enzymes. Other methods involve the chemical modification of optically active precursors. Eur. Pat. Appl. No. 95-110685 discloses a method for the preparation of optically active 3-hydroxypyrrolidine derivatives by the reduction of optically active 3-hydroxypyrrolidine-2,5-diones with activated alkali borohydrides. Another process involves the chemical modification of optically active butanoate derivatives (Eur. Pat. Appl. No. 91-303245). A microbiological method has also been reported for the preparation of (−)-(3-hydroxypyrrolidin-1-yl)-phenyl-methanone from phenyl-pyrrolidin-1-yl-methanone with the fungus *Cunninghamella verticillata* VKM F-430 (Parshikov, et al, Khimiya Geterotsiklicheskikh Soedinenii, 2: 195–199 (1992)). Another microbiological method reports the preparation of optically active N-benzyl-3-hydroxypyrrolidine by the hydroxylation of N-benzylpyrrolidine with *Pseudomonas oleovorans* Gpo1 and other bacterial species (Li et al, Tetrahedron. Asymmetry, 10: 1323–1333 (1999)).

SUMMARY OF THE INVENTION

In one embodiment, the present invention is directed to a process for the production of a compound of the formula:

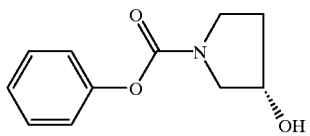

II from a compound of the formula

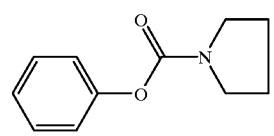

I comprising hydroxylating a compound of the formula I in the presence of at least one hydroxylating enzyme produced by a microorganism.

In a preferred embodiment, the present invention is directed to a process wherein said microorganism is selected from the group consisting of

*Aspergillus ochraceus* ATCC 18500,
*Streptomyces aureofaciens* ATCC 10762,
*Cunninghamella echinulata* v. elegans ATCC 8688b,
*Cunninghamella echinulata* v. elegans ATCC 8688a,
*Cunninghamella echinulata* v. echinulata ATCC 9244,
*Cunninghamella homothallica* ATCC 16161,
*Cunninghamella echinulata* v. elegans ATCC 36112,
*Cunninghamella echinulata* v. echinulata ATCC 36190,
*Cunninghamella echinulata* v. elegans ATCC 10028b,
*Cunninghamella echinulata* v. elegans ATCC 9245,
*Cunninghamella echinulata* v. elegans ATCC 8983,
*Cunninghamella echinulata* v. elegans ATCC 26269,
*Pithomyces cynodontis* ATCC 26150,
*Absidia glauca* ATCC 22752,
*Beauveria bassiana* ATCC 7159,
*Nocardia sp.* ATCC 53758,
*Streptomyces rimosus* ATCC 55043, and
*Streptomyces rimosus* ATCC 23955, In another embodiment, the present invention is directed to a process for the production of a compound of the formula:

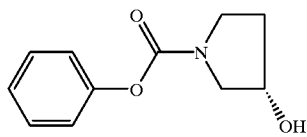

II from a compound of the formula

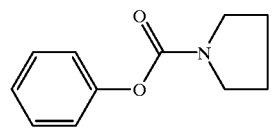

I comprising hydroxylating a compound of the formula I in the presence of at least one hydroxylating enzyme produced by a microorganism of the Cunninghamella species.

Preferred is the process wherein said Cunninghamella species is *Cunninghamella echinulata* var elegans.

Also preferred is the process wherein said *Cunninghamella echinulata* species is *Cunninghamella echinulata* var. elegans ATCC 8688b.

In another embodiment, the present invention is directed to a process for the production of a compound of the formula:

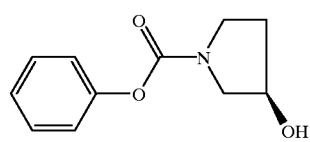

III from a compound of the formula:

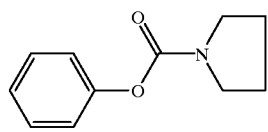

I comprising hydroxylating a compound of the formula I in the presence of at least one hydroxylating enzyme produced by a culture of a microorganism of the genus Aspergillus.

Preferred is the process wherein said Aspergillus culture is *Aspergillus flavipes*.

Also preferred is the process wherein said *Aspergillus flavipes* culture is *Aspergillus flavipes* ATCC 16795.

In another embodiment the present invention is directed to a process for the production of a compound of the formula

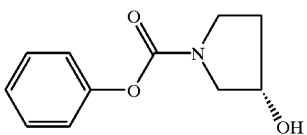

II from a compound of the formula

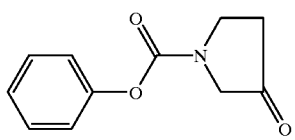

IV comprising selectively reducing a compound of the formula IV in the presence of at least one reducing enzyme produced by a culture of a microorganism of the genus Cunninghamella.

In a preferred embodiment, the present invention is directed to a process wherein said Cunninghamella is *Cunninghamella echinulata* var. elegans.

In another preferred embodiment, the present invention is directed to, a process wherein said Cunninghamella species is *Cunninghamella echinulata* var. elegans ATCC 8688b.

In another preferred embodiment, the compounds of formula II is produced from mixtures of compound II and III by a process comprising converting the compound of formula III to the compound of formula II with enzymes from *Cunninghamella echinulata*.

DETAILED DESCRIPTION OF THE INVENTION

The present invention relates to a microbiological process for the production of optically active 3-hydroxypyrrolidine derivatives. More particularly, this invention relates to a process that comprises contacting pyrrolidine-1-carboxylic acid phenylester, the compound of formula (I), with a suitable microorganism capable of hydroxylating the compound of formula (I), and recovering the optically active 3-hydroxypyrrolidine derivatives, compounds of formula (II) and (III), that are selectively formed and accumulated. Another aspect of the invention relates to a microbiological process for the production of an optically active 3-hydroxypyrrolidine derivative by the asymmetric reduction of a ketone precursor. This process comprises contacting 3-oxo-pyrrolidine-1-carboxylic acid phenyl ester (IV)

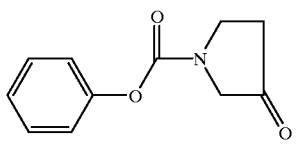

IV with a suitable microorganism capable of selectively reducing the ketone group to form and accumulate the compound of formula (II). Also disclosed is a process for the production of (II) from racemic mixtures of (II) and (III). This process comprises contacting a racemic mixture of (II) and (III) with a suitable microorganism capable of selectively converting the (R)-isomer of formula (III) to the (S)-isomer of formula (II). Optically active 3-hydroxypyrrolidine derivatives are useful intermediates for the synthesis of pharmaceutical and agrochemical compounds.

The microbiological hydroxylation of pyrrolidine-1-carboxylic acid phenylester, the compound of formula (I), to optically active 3-hydroxypyrrolidine-1-carboxylic acid phenylesters, compounds of formula (II) and (III), can be carried out by contacting the compound of formula (I) with cultures of suitable microorganisms.

In the alternative, the enzyme or enzymes can be purified or partially purified from the microorganism or cell fragments of the microorganism can be used. Immobilized cells of the microorganisms can also be used.

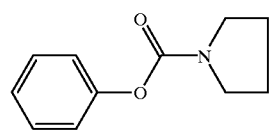

I

Contacting pyrrolidine-1-carboxylic acid phenylester, the compound of formula (I), with a culture of the microorganism *Cunninghamella echinulata* ATCC 8688b, results in the formation and accumulation of (S)-3-hydroxypyrrolidine-1-carboxylic acid phenylester, the compound of formula (II).

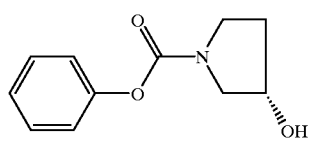

II (R)-3-Hydroxypyrrolidine-1-carboxylic acid phenylester, the compound of formula (III), is formed and accumulated by contacting pyrrolidine-1-carboxylic acid phenylester, the compound of formula (I), with a culture of the microorganism *Aspergillus flavipes* ATCC 16795.

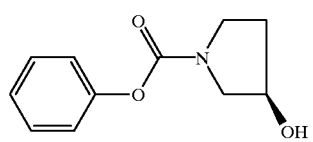

III (S)-3-Hydroxypyrrolidine-1-carboxylic acid phenylester (II) is also formed and accumulated by contacting 3-oxo-pyrrolidine-1-carboxylic acid phenyl ester (IV) with cultures of the microorganism *C. echinulata* ATCC 8688b.

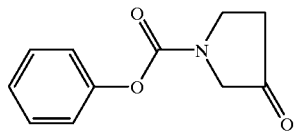

IV (S)-3-Hydroxypyrrolidine-1-carboxylic acid phenylester (II) is also formed and accumulated by contacting racemic mixtures of (I) and (III) with cultures of the microorganism *C. echinulata* ATCC 8688b.

EXAMPLE 1

Screen for Microbial Hydroxylation of Pyrrolidine-1-carboxylic acid Phenylester (I)

The capability of the microorganisms identified below to hydroxylate pyrrolidine-1-carboxylic acid phenylester (I) was identified by the methods described below. Cells of various microorganisms were grown in tubes containing 2.5 mL of dextrose, nutrisoy flour medium (2% dextrose, 0.5% nutrisoy flour, 0.5% yeast extract, 0.5% NaCl, and 0.5% $K_2HPO_4$, pH 7.0). The medium pH was adjusted prior to sterilization but was not controlled after inoculation. Individual tubes were inoculated with spores or vegetative cells (about 1% w/v of spore or vegetative cell stock culture) of various microorganisms stored as frozen glycerol suspensions and incubated at about 28° C. with agitation at 220 rpm on a rotary shaker. After about 48 hours, 0.025 mL of a 20 mg/mL solution of pyrrolidine-1-carboxylic acid phenylester, dissolved in ethanol, was added to each tube.

The tubes were incubated for about 4 days after substrate addition, after which the contents were extracted with ethyl acetate (ETOAc). The ETOAc extracts were dried under a stream of nitrogen, reconstituted in 1 mL of acetonitrile (ACN):water (1·1, v/v), and analyzed by reverse phase high performance liquid chromatography (HPLC) using an Inertsil® C8 column C column Engineering Inc, Ontario Calif., (4.6 mm internal diameter×250 mm). The analyses were performed by gradient elution using mixtures of 20 mM $NaH_2PO_4$ (pH 4.5) and ACN under the following conditions: 25% ACN from time zero to 2 minutes; 50% ACN from 2.1 minutes to 15 minutes; 1 mL/minute solvent flow rate. Under these conditions, the substrate eluted at 11.2 minutes and the alcohol products (II and II) eluted at 6.9 minutes. Extracts that contained product alcohols were dried down, reconstituted in a mixture of hexane:isopropyl alcohol (ipa), (9:1, v/v), and analyzed by HPLC on a Chiracel® OD column, (Chiral Technologies Inc Exton, Pa.) (4.6 mm internal diameter×250 mm). The Chiracel® OD analyses were performed by isocratic elution with a mixture of hexane:ipa (92:8, v/v) at a flow rate of 1 mL/minute. Under these conditions, (S)-3-hydroxypyrrolidine—carboxylic acid phenylester (II) eluted at about 36.1 minutes, and (R)-3-hydroxypyrrolidine-1-carboxylic acid phenylester (III) eluted at about 33.6 minutes. The results of these reverse phase and chiral HPLC analyses are summarized in Table 1.

TABLE 1

Microbial hydroxylation of pyrrolidine-1-carboxylic acid phenylester (I) by various microorganisms in tube fermentations

| Microorganism | % Alcohol | % ee (configuration) |
|---|---|---|
| *Cunninghamella echinulata* v. *elegans* ATCC 8688b | 39 | 62 (S) |
| *Cunninghamella echinulata* v. *elegans* ATCC 8688a | 36 | 35 (S) |
| *Cunninghamella echinulata* v. *echinulata* ATCC 9244 | 35 | 31 (S) |
| *Aspergillus ochraceus* ATCC 1008 | 33 | 35 (R) |
| *Actinomucor elegans* ATCC 6476 | 32 | 19 (R) |
| *Cunninghamella homothallica* ATCC 16161 | 32 | 36 (S) |
| *Cunninghamella echinulata* v. *elegans* ATCC 36112 | 28 | 38 (S) |
| *Aspergillus ochraceus* ATCC 22947 | 28 | 32 (R) |
| *Cunninghamella echinulata* v. *echinulata* ATCC 36190 | 24 | 33 (S) |
| *Cunninghamella echinulata* v. *elegans* ATCC 10028b | 24 | 53 (S) |
| *Cunninghamella echinulata* v. *elegans* ATCC 9245 | 22 | 45 (S) |
| *Cunninghamella echinulata* v. *elegans* ATCC 8983 | 21 | 48 (S) |
| *Cunninghamella echinulata* v. *elegans* ATCC 26269 | 20 | 32 (S) |
| *Streptomyces coelicolor* ATCC 10147 | 19 | 33 (R) |
| *Pithomyces cynodontis* ATCC 26150 | 18 | 81 (S) |
| *Absidia glauca* ATCC 22752 | 17 | 34 (S) |
| *Beauveria bassiana* ATCC 7159 | 15 | 39 (S) |
| *Nocardia sp.* ATCC 53758 | 15 | 90 (S) |
| *Streptomyces rimosus* ATCC 55043 | 15 | 79 (S) |
| *Streptomyces rimosus* ATCC 23955 | 14 | 77 (S) |
| *Aspergillus flavipes* ATCC 16795 | 13 | 94 (R) |
| *Nocardia sp.* NRRL 5646 | 12 | 18 (R) |
| *Aspergillus ochraceus* ATCC 18500 | 12 | 30 (S) |
| *Absidia repens* ATCC 14849 | 11 | 9 (R) |
| *Streptomyces aureofaciens* ATCC 10762 | 11 | 75 (S) |

EXAMPLE 2

Microbial Hydroxylation of Pyrrolidine-1-carboxylic acid Phenylester (I) by *Cunninghamella echinulata* ATCC 8688b in Various Media

*C. echinulata* ATCC 8688b was grown in glass tubes (125 mm×16 mm internal diameter) containing 2.5 mL aliquots of five different media, prepared as described below Medium 1 was prepared with dextrose and nutrisoy flour as described in example 1 Medium 2 was prepared with cornsteep liquor (4%) and dextrose (2%) and adjusted to pH 4.85 before sterilization. Medium 3 was prepared with cornsteep solids (4%) and dextrose (2%) and adjusted to pH 4.85 before sterilization. Medium 4 was prepared with Pharmamedia® (2%) (Traders Protein Memphis Tenn.) and dextrose (2%) and adjusted to pH 7.2 before sterilization Medium 5 was prepared with malt extract (1%), dextrose (1%), peptone (0.5%), and yeast extract (0.2%) and adjusted to pH 7.0 before sterilization. Tubes containing growth medium 1, 3, 4, and 5 were inoculated with spores of C. echinulata ATCC 8688b and incubated at 28° C. with agitation (220 rpm). After about 48 hours of growth, 0.025 mL of a 60 mg/mL ethanol solution of pyrrolidine-1-carboxylic acid phenylester (I) was added to each tube. The tubes were incubated for about 10 days after substrate addition, after which the contents were extracted with ETOAc. The ETOAc extracts were dried under a stream of nitrogen, reconstituted in a mixture of ACN:water (1:1, v/v), and analyzed by reverse phase and chiral HPLC as described in Example 1. Tubes containing growth medium 2 were treated in a manner analogous to that described for media 1, 3, 4, and 5, except that substrate was added at inoculation time. The results of reverse phase and chiral HPLC assays are summarized in Table 2.

TABLE 2

Microbial hydroxylation of pyrrolidine-1-carboxylic acid phenylester (I) by C. echinulata ATCC 8688b in tube cultures with various media.

| Medium | Substrate (g/L) | % Alcohol | % ee (S) |
|--------|----------------|-----------|----------|
| 1 | 0.6 | 46 | 74 |
| 2 | 0.6 | 56 | 91 |
| 3 | 0.6 | 27 | 82 |
| 4 | 0.6 | 37 | 86 |
| 5 | 0.6 | 43 | 7 |

EXAMPLE 3

Microbial Hydroxylation of Pyrrolidine-1-carboxylic acid Phenylester (I) in flask culture of Cunninghamella echinulata ATCC 8688b Six Fernbach flasks, each containing 0.5 L of medium 2 as described in Exemple 2 were inoculated with spores of C. echinulata ATCC 8688b and incubated at 29° C. on a rotary shaker (220 rpm). After 24 hours, 5 mL of a 60 mg/mL ethanol solution of pyrrolidine-1-carboxylic acid phenylester (II) were added to each flask, and incubated for 16 more days. The bioconversion was monitored in two of the six flasks (flasks A and B) by removing samples of fermentation broth, extracting with ETOAc, and analyzing the extracts by reverse phase and chiral HPLC as described in Example 1. The results of these HPLC analyses are summarized in Table 3. The contents of all six flasks were pooled after the 16 days incubation and filtered through a triple-layer of cheesecloth to remove cells. The filtrate was then stirred with 50 g of Amberlite® XAD-16 resin (Rohm and Haas, Philadelphia, Pa.) for 4.5 hours at 21° C. The resin was collected onto filter paper and washed with 0.8 L of ETOAc. The ETOAc extract was washed with water, dried with anhydrous magnesium sulfate, and concentrated under reduced pressure to give 0.93 g of crude product. The crude product was applied to a 5 g silica Seppak® cartridge (Waters Corporation, Milford, Mass.) and eluted with mixtures of ETOAc and hexane, (2:3, 1:1) and the fractions containing the desired product were concentrated under reduced pressure to give 0.64 g (33% yield, 89% ee) of (S)-3-hydroxypyrrolidine-1-carboxylic acid phenylester (II).

TABLE 3

Microbial hydroxylation of pyrrolidine-1-carboxylic acid phenylester (I) in flask cultures of C. echinulata ATCC 8688b.

| | Flask A | | Flask B | |
|---|---|---|---|---|
| Time (days) | % Alcohol | % ee | % Alcohol | % ee |
| 2 | 37 | 20 (R) | 35 | 18 (R) |
| 4 | 56 | 12 (R) | 54 | 8 (S) |
| 6 | 61 | 3 (S) | 58 | 11 (S) |
| 8 | 63 | 23 (S) | 56 | 30 (S) |
| 12 | 58 | 72 (S) | 50 | 67 (S) |
| 14 | 54 | 82 (S) | 48 | 75 (S) |
| 16 | 51 | 88 (S) | 47 | 82 (S) |

EXAMPLE 4

Microbial Hydroxylation of Pyrrolidine-1-carboxylic acid Phenylester (I) in fermentor cultures of Cunninghamella echinulata ATCC 8688b Three Fernbach flasks each containing 0.5 L of medium 2 as described in Example 2 were inoculated with spores of C. echinulata ATCC 8688b and incubated at 29° C. on a rotary shaker (220 rpm). After about 24 hours, the contents of the three flasks were combined and used to inoculate two fermentors, each containing 8 L of medium 2. Fermentors (Fermentors A and B) were operated at 29° C. with 600 rpm agitation and 8 liter per minute aeration. The pH was controlled between 6 and 7. After 24 hours, the bioconversion was started by adding 4.8 g of substrate (I), dissolved in 20 mL ethanol, to each fermentor. The bioconversion was followed by removing samples, extracting with ETOAc, and analyzing by reverse phase and chiral HPLC as described in Example 1. The results of these HPLC analyses are summarized in Table 4. About 9 days after substrate addition, the contents of the fermentors were pooled and filtered through a triple-layer of cheesecloth. The filtrate was passed through a column containing about 500 g of XAD-16 resin. The resin was then washed with 1 L of water and eluted with 6 L of ETOAc. The ETOAc eluates were washed with water, dried over anhydrous magnesium sulfate, and concentrated under reduced pressure to give the crude product. The crude product was applied to a silica flash cartridge (Biotage Herts SGI3 7NW ENGLAND) and eluted with mixtures of ETOAc and hexanes, (2:3, 1·1) beginning with 10% ETOAc, and increasing in 10% increments to 80% ETOAc. Fractions eluted with 60–80% ETOAc were combined and concentrated under reduced pressure to give 2.9 g (28% yield, 88% ee) of (S)-3-hydroxypyrrolidine-1-carboxylic acid phenylester (II).

TABLE 4

Microbial hydroxylation of pyrrolidine-1-carboxylic acid phenylester (I) by C. echinulata ATCC 8688b in fermentor cultures.

| | Fermentor A | | Fermentor B | |
|---|---|---|---|---|
| Time (days) | % Alcohol | % ee | % Alcohol | % ee |
| 1 | 38 | 21 (R) | 40 | 21 (R) |
| 3 | 52 | 24 (S) | 51 | 32 (S) |
| 5 | 44 | 65 (S) | 44 | 68 (S) |
| 7 | 38 | 81 (S) | 39 | 82 (S) |
| 9 | 37 | 94 (S) | 32 | 94 (S) |

EXAMPLE 5

Microbial Hydroxylation of Pyrrolidine-1-carboxylic acid phenylester (I) in tube cultures of *Aspergillus flavipes* ATCC 16795 Four tubes containing 2.5 ml of medium 2 (Example 2) were inoculated with spores of *A flavipes* ATCC 16795 and incubated at 29° C. on a rotary shaker (210 rpm). After about 24 hours, 0.025 mL of a 20 mg/mL ethanol solution of pyrrolidine-1-carboxylic acid phenylester (I) was added to two tubes, and 0.025 mL of a 50 mg/mL ethanol solution of (I) was added to the remaining two tubes. The tubes were incubated for about 10 days after substrate addition. after which the contents were extracted with ETOAc. The ETOAc extracts were dried under a stream of nitrogen, reconstituted in a mixture of ACN:water (4:1, v/v), and analyzed by reverse phase and chiral HPLC as described in Example 1. The results of these HPLC analyses are summarized in Table 5.

TABLE 5

Microbial hydroxylation of pyrrolidine-1-carboxylic acid phenylester (I) by *A. flavipes* ATCC 16795 in tube cultures.

| Substrate (g/L) | % Alcohol | % ee (R) |
|---|---|---|
| 0.2 | 50 | 92 |
| 0.5 | 15 | 89 |

EXAMPLE 6

Microbial reduction of 3-oxo-pyrrolidine-1-carboxylic acid phenylester (IV) in tube cultures of *Cunninghamella echinulata* ATCC 8688b Two tubes containing 2.5 ml of medium 2 as described in Example 2 were inoculated with spores of *C. echinulata* ATCC 8688b and incubated at 29° C. on a rotary shaker (210 rpm). After about 24 hours, 0.025 mL of a 20 mg/mL ethanol solution of 3-oxo-pyrrolidine-1-carboxylic acid phenylester (IV) was added to each tube. The tubes were incubated for about 6 days after substrate addition, after which the contents were extracted with ETOAc. The ETOAc extracts were dried under a stream of nitrogen, reconstituted in a mixture of ACN:water (4:1, v/v), and analyzed by reverse phase and chiral HPLC as described in example 1. The results of these HPLC analyses revealed the conversion of IV to I with a yield of 79% and an ee of greater than 99%.

EXAMPLE 7

Deracemization of (+/−)-3-hydroxy-pyrrolidine-1-carboxylic acid phenylester in tube cultures of *Cunninghamella echinulata* ATCC 8688b Twenty four tubes containing 2.5 ml of medium 2 as described in Example 2 were inoculated with spores of *C. echinulata* ATCC 8688b and incubated at 29° C. on a rotary shaker (210 rpm). After about 24 hours, 0.025 mL of a 60 mg/mL ethanol solution of (+/−)-3-hydroxy-pyrrolidine-1-carboxylic acid phenylester was added to twelve tubes (treatment A), and 0.025 mL of a 100 mg/mL ethanol solution of (+/−)-3-hydroxy-pyrrolidine-1-carboxylic acid phenylester was added to the remaining twelve tubes (treatment B). The tubes were incubated at 29° C. and agitated on a rotary shaker at 210 rpm. Two tubes were harvested from each treatment after 2, 4, 6, 8, 10, and 12 days incubation and the contents extracted with ETOAc. The ETOAc extracts were dried under a stream of nitrogen, reconstituted in a mixture of ACN:water (4:1, v/v), and analyzed by reverse phase and chiral HPLC as described in example 1. The results of these HPLC analyses are summarized in Table 6.

TABLE 6

Microbial deracemization of (+/−)-3-hydroxy-pyrrolidine-1-carboxylic acid phenylester by *C. echinulata* ATCC 8688b in tube cultures.

| Time (days) | Treatment A (0.6 g/L substrate) | | Treatment B (1.0 g/L substrate) | |
|---|---|---|---|---|
| | % Alcohol | % ee (S) | % Alcohol | % ee (S) |
| 2 | 94 | 6 | 90 | 6 |
| 4 | 91 | 19 | 85 | 18 |
| 6 | 88 | 41 | 86 | 38 |
| 8 | 81 | 70 | 79 | 65 |
| 10 | 72 | 90 | 70 | 81 |
| 12 | 62 | 87 | 60 | 89 |

What is claimed is:

1. A process for the production of a compound of the formula

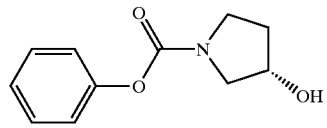

II from a compound of the formula

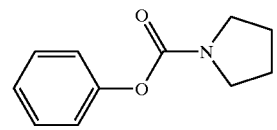

I comprising hydroxylating a compound of the formula I in the presence of a suitable microorganism, wherein said microorganism comprises at least one suitable hydroxylating enzyme.

2. A process according to claim 1 wherein said microorganism is selected from the group consisting of

*Aspergillus ochraceus* ATCC 18500,

*Streptomyces aureofaciens* ATCC 10762,

*Cunninghamella echinulata* v. elegans ATCC 8688b,

*Cunninghamella echinulata* v. elegans ATCC 8688a,

*Cunninghamella echinulata* v. echinulata ATCC 9244,

*Cunninghamella homothallica* ATCC 16161,

*Cunninghamella echinulata* v. elegans ATCC 36112,

*Cunninghamella echinulata* v. echinulata ATCC 36190,

*Cunninghamella echinulata* v. elegans ATCC 10028b,

*Cunninghamella echinulata* v. elegans ATCC 9245,

*Cunninghamella echinulata* v. elegans ATCC 8983,

*Cunninghamella echinulata* v. elegans ATCC 26269,

*Pithomyces cynodontis* ATCC 26150,

*Absidia glauca* ATCC 22752,

*Beauveria bassiana* ATCC 7159,

*Nocardia* sp. ATCC 53758,

*Streptomyces rimosus* ATCC 55043, and

*Streptomyces rimosus* ATCC 23955.

3. A process for the production of a compound of the formula

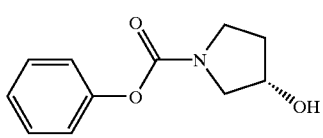
II from a compound the formula

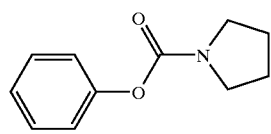
I comprising hydroxylating a compound of the formula I in the presence of a microorganism of the genus Cunninghamella, wherein said microorganism comprises at least one suitable hydroxylating enzyme.

4. A process according to claim 3 wherein said Cunninghamella is *Cunninghamella echinulata* var. elegans.

5. A process according to claim 4 wherein said *Cunninghamella echinulata* species is *Cunninghamella echinulata* var. elegans ATCC 8688b.

6. A process for the production of a compound of the formula

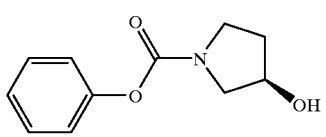
III from a compound of the formula

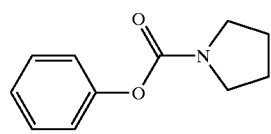
I comprising hydroxylating a compound of the formula I in the presence of a microorganism of the genus Aspergillus, wherein said microorganism comprises at least one suitable hydroxylating enzyme.

7. A process according to claim 6 wherein said Aspergillus is *Aspergillus flavipes*.

8. A process according to claim 7 wherein said *Aspergillus flavipes* is *Aspergillus flavipes* ATCC 16795.

9. A process for the production of a compound of the formula

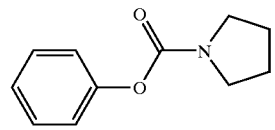
I from a compound of the formula

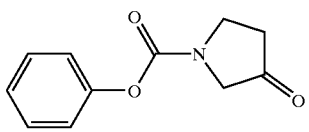
IV comprising selectively reducing a compound of the formula IV in the presence of a microorganism of the genus Cunninghamella, wherein said microorganism comprises at least one suitable reducing enzyme.

10. A process according to claims wherein said Cunninghamella is *Cunninghamella echinulata*.

11. A process according to claim 10 wherein said Cunninghamella is *Cunninghamella echinulata* ATCC 8688b.

12. A process for the production of a compound of the formula

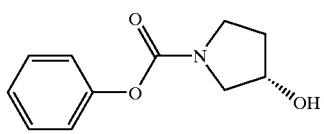
II from a mixture of compounds to the formula

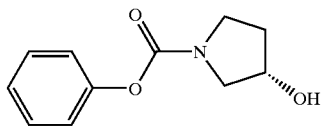
II

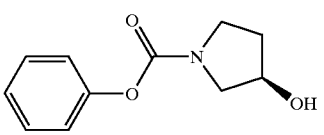
III comprising converting the compound of formula II in the presence of a suitable microorganism, wherein said microorganism comprises at least one suitable enzyme.

13. A process according to claim 12 wherein said microorganism is *Cunninghamella echinulata* var. elegans ATCC: 8688b.

* * * * *